(12) United States Patent
Johnston et al.

(10) Patent No.: US 6,553,930 B1
(45) Date of Patent: Apr. 29, 2003

(54) TAMPER-INDICATING DEVICE HAVING A GLASS BODY

(75) Inventors: Roger G. Johnston, Los Alamos, NM (US); Anthony R. E. Garcia, Espanola, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/614,266

(22) Filed: Jul. 12, 2000

(51) Int. Cl.[7] .................................................. G01L 5/00
(52) U.S. Cl. ..................................... 116/212; 116/200
(58) Field of Search ............................... 116/212, 200, 116/203, 206

(56) References Cited

U.S. PATENT DOCUMENTS

| | | | | |
|---|---|---|---|---|
| 1,516,454 A | * | 11/1924 | Norton ........................ 116/206 |
| 3,463,532 A | * | 8/1969 | Chidley et al. ............. 116/206 |
| 3,822,895 A | * | 7/1974 | Ochiai .................. 280/150 AB |
| 3,869,609 A | | 3/1975 | Jehenson et al. ........... 250/272 |
| 3,899,295 A | * | 8/1975 | Halpern .................. 23/253 TP |
| 3,938,465 A | * | 2/1976 | Lyons ...................... 116/63 P |
| 3,946,611 A | * | 3/1976 | Larson ......................... 73/356 |
| 3,996,007 A | * | 12/1976 | Fang et al. ............. 23/253 TP |
| 4,106,849 A | * | 8/1978 | Stieff ...................... 350/96.24 |
| 4,130,341 A | * | 12/1978 | Stieff ........................ 350/96.2 |
| 4,424,911 A | * | 1/1984 | Resnick ....................... 215/256 |
| 4,511,052 A | | 4/1985 | Klein et al. .................. 215/230 |
| 4,601,404 A | | 7/1986 | Shivers ....................... 215/230 |
| 4,826,027 A | * | 5/1989 | Nilson ....................... 116/200 |
| 4,984,701 A | * | 1/1991 | Margaria ..................... 215/256 |
| 5,617,812 A | * | 4/1997 | Balderson et al. .......... 116/206 |
| 6,206,432 B1 | * | 3/2001 | Kamiyama .................... 285/81 |
| 6,244,487 B1 | * | 6/2001 | Murray ......................... 225/93 |
| 6,394,022 B1 | * | 5/2002 | Johnston et al. ............ 116/206 |
| 2001/0003150 A1 | * | 6/2001 | Imbert ......................... 604/256 |

OTHER PUBLICATIONS

Roger G. Johnston, Anthony R.E. Garcia, "Tamper Detection for Waste Managers," LA–UR–98–4874, 10.91.
Roger G. Johnston, "The Real Deal on Seals Improving Tamper Detection," LAUR–96–3938, 10.91.
Fay V. Tooley, "Handbook of Glass Manufacture," Ogden Publishing Company, New York 36, NY, pp. 391–420, 02.1953.

* cited by examiner

Primary Examiner—Diego Gutierrez
Assistant Examiner—Gail Verbitsky
(74) Attorney, Agent, or Firm—Samuel L. Borkowsky

(57) ABSTRACT

A tamper-indicating device is described. The device has a first glass body member and a second glass body member that are attached to each other through a hasp. The glass body members of the device can be tempered. The body members can be configured with hollow volumes into which powders, microparticles, liquids, gels, or combinations thereof are sealed. The choice, the amount, and the location of these materials can produce a visible, band pattern to provide each body member with a unique fingerprint identifier, which makes it extremely difficult to repair or replace once it is damaged in order to avoid tamper detection.

18 Claims, 5 Drawing Sheets

TAMPER-INDICATING DEVICE HAVING A GLASS BODY

This invention was made with government support under Contract No. W-7405-ENG-36 awarded by the U.S. Department of Energy to The Regents of the University of California. The U.S. government has certain rights in the invention.

FIELD OF THE INVENTION

The present invention relates generally to tamper-indicating devices and, more particularly, to a tamper-indicating device that is used with a hasp for sealing a container.

BACKGROUND OF THE INVENTION

Tamper-indicating devices are widely used to detect tampering or unauthorized entry into a container, building, railcar, etc. These devices include frangible films, pressure sensitive adhesive tapes, crimped cables, electronic systems that continuously monitor changes in electric cables or fiber optic bundles, and other devices that are intended to display irreversible damage or changes when manipulated. They are used to detect theft of items during transportation and warehousing. They are used in retail and corporate security applications such as recordkeeping and inventory control. They are used in law enforcement and national security applications such as counterterrorism, counterintelligence, and protection of specimens for drug testing. They are used in a variety of defense applications such managing hazardous and nuclear materials and weapons. They are used in the health industry to protect instrument calibrations, medical products, blood bank supplies, and pharmaceuticals. They are used to protect records in the banking industry. They are used to detect and prevent ballot box fraud during elections. In short, these are extremely important devices that are designed with the intention of providing unambiguous and non-erasable evidence of tampering and unauthorized entry.

A tamper-indicating device has been defeated when it has been deactivated and activated, removed and replaced, opened and closed, etc. while leaving no detectable evidence of manipulation. Traditional tamper-indicating devices attempt to provide physical, electronic, or some other type of evidence of tampering. Unfortunately, this evidence can often be erased easily and quickly. Intrusion alarm systems for warehouses, for example, that send an alarm signal in real-time to a security headquarters to provide an indication of potential tampering, are often easily defeated by deactivating them prior to a break-in. Tamper-indicating devices that are damaged during a tampering activity can also be defeated if the damage is repaired, or if the device is replaced with a counterfeit that confuses the repaired or replaced device with the original. Further discussion of tamper detection can be found in the following papers, the teachings of which are incorporated by reference: R. G Johnston et al. in "Tamper Detection for Waste Managers," Proceedings of Waste Management '99, (Feb. 28–Mar. 4, 1999, Tucson, Ariz.) p. 12/25-1 to 12/25-11; and R. G. Johnston in "The Real Deal on Seals, Improving Tamper Detection," Security Management, vol. 41 (1997) p. 93–100.

Clearly, tamper-indicating devices that are difficult to defeat are highly desirable. Therefore, an object of the present invention is a tamper-indicating device that is difficult to defeat.

Another object of the invention is a tamper-indicating device that provides a permanent record of tamper-indicating activity.

Another object of the present invention is tamper-indicating device that can be used with a hasp to provide a container, building, railcar, etc. with a seal.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the invention includes a tamper-indicating device having a cylindrical body with a first end portion, a second end portion, and a middle portion. The middle portion has a smaller diameter than either the first end portion or the second end portion.

The device can include an internal chamber containing materials such as powder, liquid, gel, or combinations thereof. If sufficient stress is applied to the device, then the body fractures and the materials inside the chamber are released and mixed.

BRIEF DESCRIPTION OF THE DRAWINGS

The accompanying drawings, which are incorporated in and form a part of the specification, illustrate embodiments of the present invention and, together with the description, serve to explain the principles of the invention. In the Figures.

DETAILED DESCRIPTION OF THE INVENTION

Briefly, the invention includes a tamper-indicating device that can be installed through a hasp to seal a container, truck door, railcar, etc. to provide a seal. The invention has a transparent or translucent glass body with many desirable attributes of glass: it is inexpensive, has excellent resistance to solvents and oxidation, excellent environmental durability, and a long shelf life. It is very strong, yet can fail via brittle fracture, relatively lightweight, and can be tempered to store enormous stresses that can be released when it experiences mechanical damage such as being cut or drilled into. Reference will now be made to the present preferred embodiments of the invention, examples of which are illustrated in the accompanying drawings. Similar or identical structure is identified using identical callouts.

Figure 1:
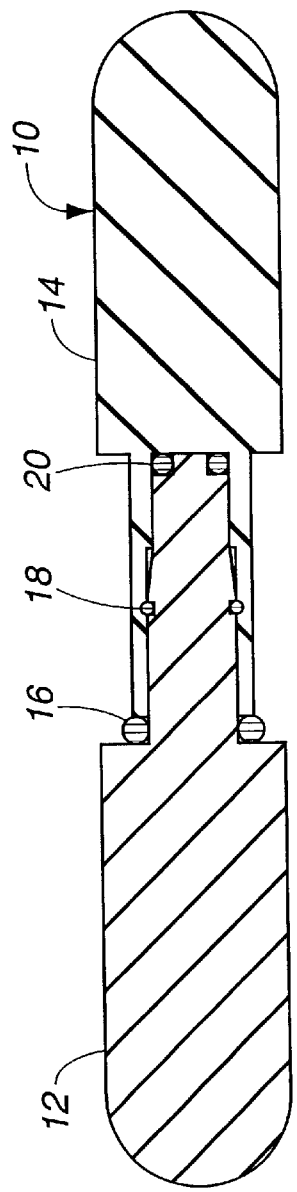
FIG. 1 shows a cross-sectional side view of an assembled embodiment of the present invention.
Figure 2:
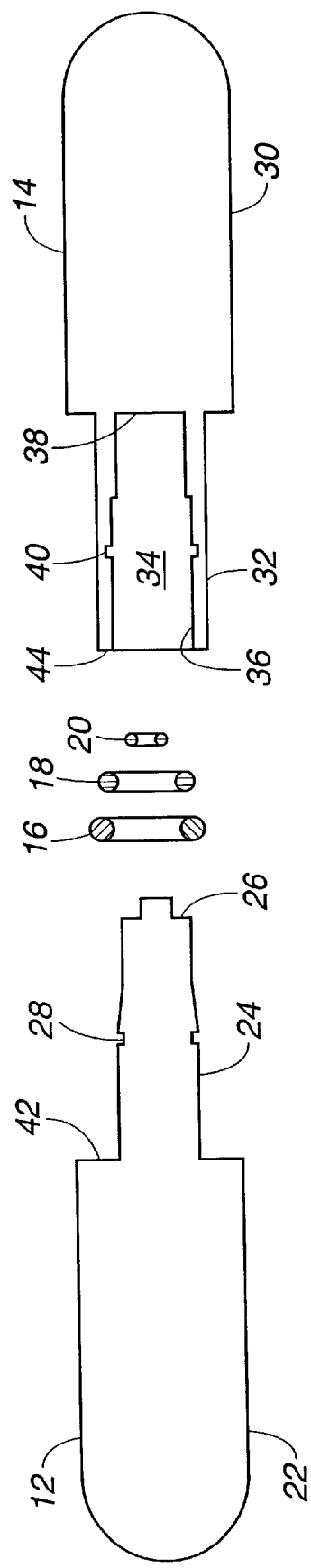
FIG. 2 shows an exploded view of the embodiment of FIG. 1.

FIG. 1 shows a cross-sectional side view of an embodiment of the present invention, and FIG. 2 shows an exploded side view of the same embodiment. Device 10 is cylindrical and includes first body member 12, second body member 14, first sealing member 16, locking ring 18, and second sealing member 20. First body member 12 has a first end portion 22 and a narrower second portion 24, and a still narrower cylindrical portion 26, extending from second portion and adapted to receive second sealing member 20. Circumferential recess 28 within second end portion 24 is adapted to receive locking ring 18. Second body member 14 includes a first end portion 30 and a narrower second end portion 32 extending from first end portion 30. Second body member 14 includes cylindrical hollow portion 34 within second end portion 32 and having cylindrical inner wall 36 and end wall 38. Second body member 14 includes annular recess 40 along inner surface 36 adapted to receive locking ring 18. Inner walls 36 and 38 and recesses 28 and 40 are configured so that when narrow end portion 24 of first body member 12 is inserted into hollow portion 34 of second body member 14, recesses 28 and 40 are in alignment. This way, locking ring 18 can irreversibly engage both recesses 28 and 40, which provides the mechanism of attachment of first body member 12 to second body member 14. Device 10 is assembled by passing first sealing member 16 through narrow portion 24 until it contacts outer wall 42 of first body member 12, then inserting locking ring 18 into recess 28, then positioning second sealing member 20 around cylindrical portion 26. First body member 12 is then inserted into hollow portion 34 of second body member 14 until locking ring 18 engages recess 40. First sealing member 16 will then form a seal with end 44 of second body member 14, and second sealing member 20 will form a seal with walls 36 and 38 of second member 14. The function of sealing members 16 and 20 is to keep device 10 air-tight so any internal pressure will not be released as long as device 10 is intact, and also to prevent water, humidity, and dirt from entering the device.

Body members 12 and 14 are preferably made from any hard, brittle, amorphous glass, such as a metal silicate, calcium silicate or sodium silicate for example. Glasses are hard, non-crystalline, inorganic, usually transparent or translucent, brittle materials that are made by fusing silicates and sometimes borates or phosphates, with certain basic inorganic oxides. After these materials are fused, the product is cooled rapidly to prevent crystallization. Glasses lack a regular crystal structure with regular crystal planes, and the lack of these planes allows glass body members 12 and 14 to fracture isotropically. Glasses are preferred materials because their strength and level of internal stress can be adjusted by known glass tempering methods that generally involve cooling the glass quickly and in a controlled manner from a temperature higher than the annealing temperature of the glass. The differential rates of cooling and spatial thermal gradients that result from tempering provide regions of stored internal compression and tension in the glass.

Sealing members 16 and 20 can be made from flexible materials such as plastics and rubbers. First sealing member 16 is preferably a compressible o-ring or gasket. Locking ring 18 is preferably a metal retaining or locking ring. Second sealing member 20 is preferably an o-ring.

Device 10 may also include serial numbers, dyes, reflective particles, or other unique fingerprint identifiers to aid in identifying the device. These identifiers can be embedded inside the glass, etched onto the surface of the device, or inserted into hollow portion 34, etc.

Figure 3:
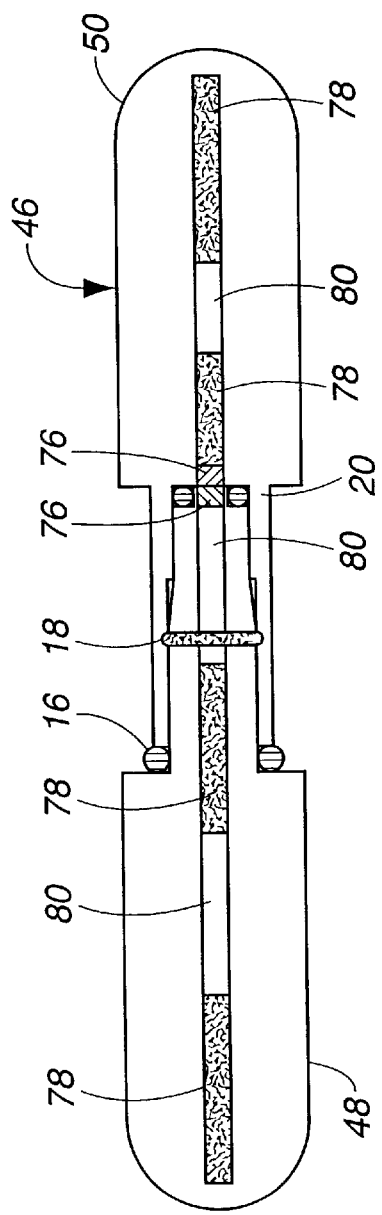
FIG. 3 shows a perspective side view of a second assembled embodiment of the present invention.
Figure 4:
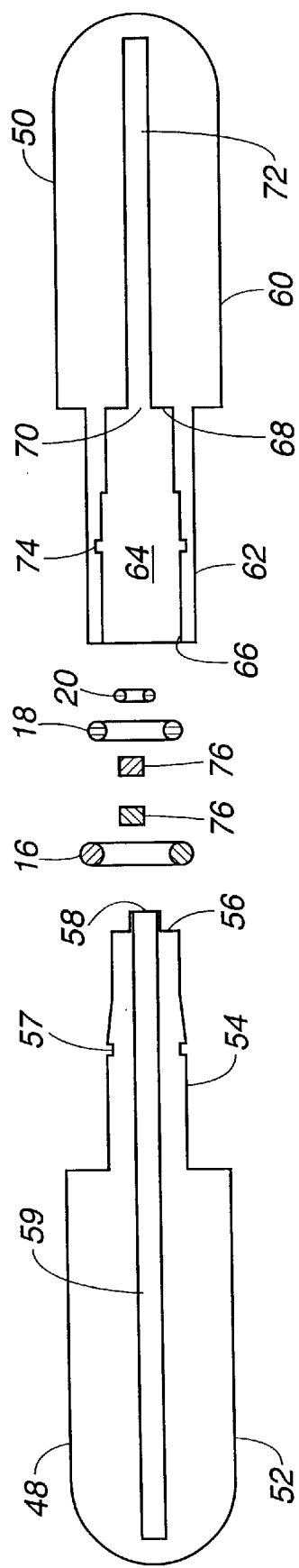
FIG. 4 shows a partially exploded side view of the embodiment of FIG. 4.

FIG. 3 shows a cross-sectional side view of a second embodiment of the present invention, and FIG. 4 shows an exploded view of the second embodiment of FIG. 3. Device 46 is cylindrical and includes transparent first body member 48 and transparent second body member 50. As can be seen by comparing FIG. 4 with FIG. 2, first body member 48 of device 46 and first body member 12 of device 10 are similar in shape. Second body member 14 of device 10 and second body member 50 of device 46 are also similar in shape. Device 46 also includes first sealing member 16, locking ring 18, and second sealing member 20. First body member 48 has a first end portion 52 and a narrower second portion 54, and a still narrower third portion 56, extending from second portion and adapted to receive second sealing member 20. Circumferential recess 57 within second end portion 54 is adapted to receive locking ring 18. Opening 58 at cylindrical portion 56 extends inward to hollow portion 59 inside body member 48 into which is placed powder, liquid, gel, or combinations thereof.

Second body member 50 includes a first end portion 60 and a narrower second end portion 62 extending from first end portion 60. Second end portion is hollow, with volume 64 defined by inner cylindrical wall 66 and end wall 68. An opening 70 in end wall 68 leads to hollow portion 72 in first end portion 60, into which powder, liquid, gel, or combinations thereof are placed. Hollow portions 59 and 72 can be coaxial with the long axis of the device, as shown in the Figures, or can be skewed relative to the long axis. Annular recess 74 along inner surface 66 is adapted to receive locking ring 18. Inner walls 66 and 68 and recesses 57 and 74 are configured so that when narrow end portion 54 of first body member 48 is inserted into hollow portion 64 of second body member 50, recesses 57 and 74 are in alignment. This way, locking ring 18 can engage both recesses 57 and 74, which provides the mechanism of attachment of first body member 48 to second body member 50.

Device 46 is assembled by first charging volume 59 with a desired material or combination of materials and then sealing opening 58 with plug 76. Volume 72 of body member 50 is similarly charged with a powder, liquid, gel, or combination thereof and then sealed with plug 76. Sealed body members 48 and 50 can now be joined as previously described for body members 12 and 14 of device 10.

The assembled embodiment of FIG. 3 includes a plurality of alternating bands of a first material 78 and a second material 80; carefully introducing a first material and then a second material produces these bands. FIG. 3 shows the invention with seven bands. Plugs 76 are then used to seal openings 58 and 70 to prevent the band materials from mixing. Clearly, many different band combinations are possible by altering the widths of bands, the number of bands, the materials used for each band, the number of different materials used, etc. After body members 48 and 50 are irreversibly connected, device 46 is effectively a single piece body with an internal band pattern identifier. Each device can be produced with this unique fingerprint identifier. To take full advantage of the identifier, device 46 should be used with hasps that do not block a view of the bands. A photograph, digital image, or other type of image of the device can be produced after sealing the bands in place inside the device. This image can be used afterward in direct comparison with the device after attachment to aid in tamper-detection. If each seal were made using a different band pattern, this may be necessary. Alternatively, a small glass capillary tube having bands identical to that of the device can be prepared and later used for comparison to detect evidence of tampering or counterfeiting.

Liquids, gels, solids, or combinations of any of these can be used to provide the band pattern. Liquids, gels, and solids can be in the form of nanoparticles, microparticles, powders, etc. Adjacent liquid bands are possible if the liquids are non-miscible to prevent mixing and band destruction. A polar liquid such as ethanol, for example, can be used to form one set of bands while a non-polar liquid such as hexane can be used to form the other set of bands. Either colorless or colored liquids can be used. Liquids are less preferred than solids since liquids can potentially be frozen into place under sufficiently cold conditions, thereby preserving a band pattern after fracture of the surrounding glass body.

Plugs 76 include glass, metal, plastic, and wax membranes that are sealed inside the device to preserve the band structure prior to use. Epoxy materials and other polymers or combinations that harden to produce a non-movable barrier that prevents band mixing can also be used. Preferably, plugs 76 are permeable to gas to allow pressure equalization through the interior of the device.

Powders and microparticles and nanoparticles are preferred materials used for making band patterns. They should be packed loosely enough so that they can flow easily after device fracture during tampering. They can be distributed inside hollow portions 59 and 72 by using a rod, by tapping the body member into which they are placed, by subjecting the body member to centrifugation, or by other methods.

The properties of the glass of device 46 can be tuned by known glass tempering methods that allow it to fracture in an unpredictable manner for a predetermined threshold level of mechanical disturbance and/or surface damage that arises during a tampering activity, as previously described for device 10.

Figure 5:
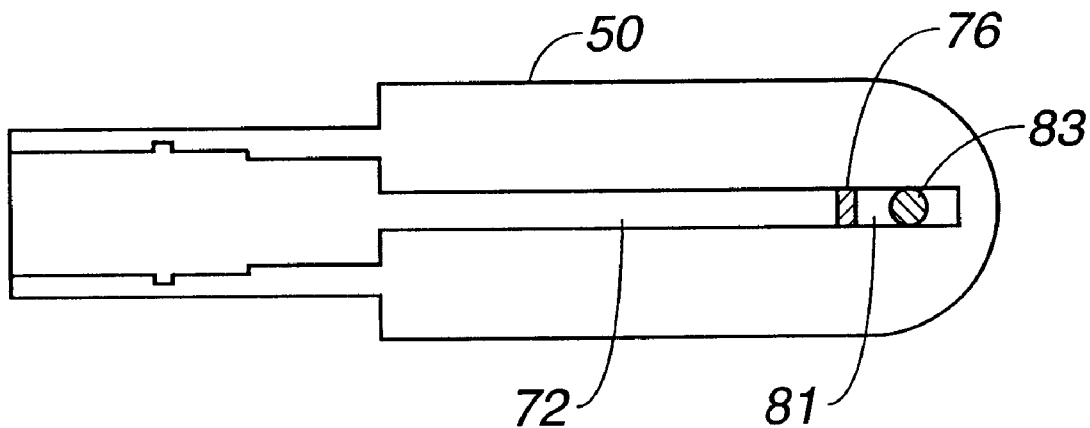
FIG. 5 shows a perspective side view of a body member with an internal coil spring held in place using a retaining ring.

Device 46 can also include optional means for generating internal pressure to aid in launching and mixing bands when device 46 fractures during a tampering effort. Fracture of the glass body and release of the internal pressure results in band mixing, which makes it nearly impossible to recreate the original band pattern. FIG. 5 shows body member 50 with pressurized chamber 81 produced by placing dry ice 83, i.e. solid $CO_2$, inside hollow portion 72, sealing the hollow portion with sealing member 76, and allowing the dry ice to sublime. A positive pressure can also be created inside the device by cooling body member 48 and/or body member 50 prior to use. When the device comes to thermal equilibrium with the environment, the pressure inside the device will be higher than the pressure outside. If cooled, for example, from room temperature to about 0° C., −78° C., or −196° C. prior to use, differential positive pressures of about 1 psi, 5 psi, and 11 psi are generated. Conversely, heating body member 48 and/or body member 50 can create a negative differential pressure, i.e. a partial vacuum. Heating from room temperature to about 100° C., prior to use, a negative differential pressure of about 3.5 psi is generated.

Figure 6:
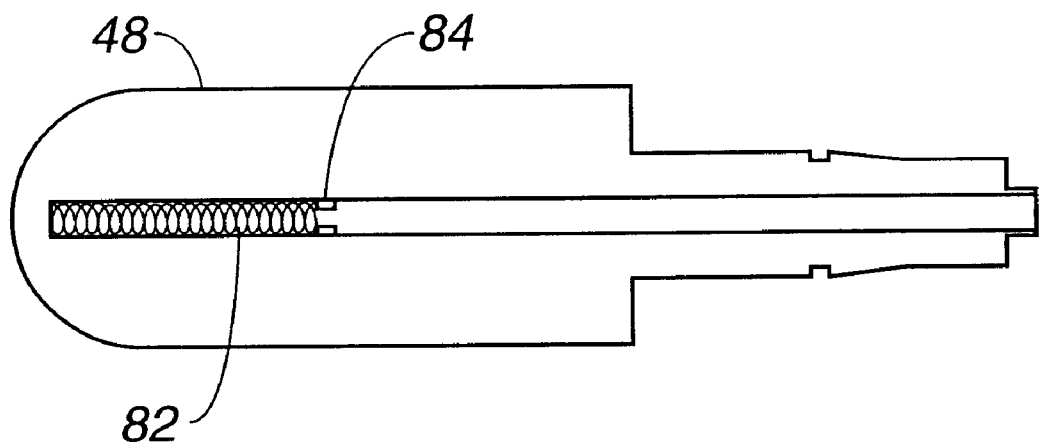
FIG. 6 shows a perspective side view of a body member of the invention having gas pressure generating means.

A compressed spring inside the device also increases band mixing when the device fractures after a tampering effort. FIG. 6 shows a perspective side view of body member 48 including internal coiled spring 82 held in place by retaining ring 84.

Figure 7:
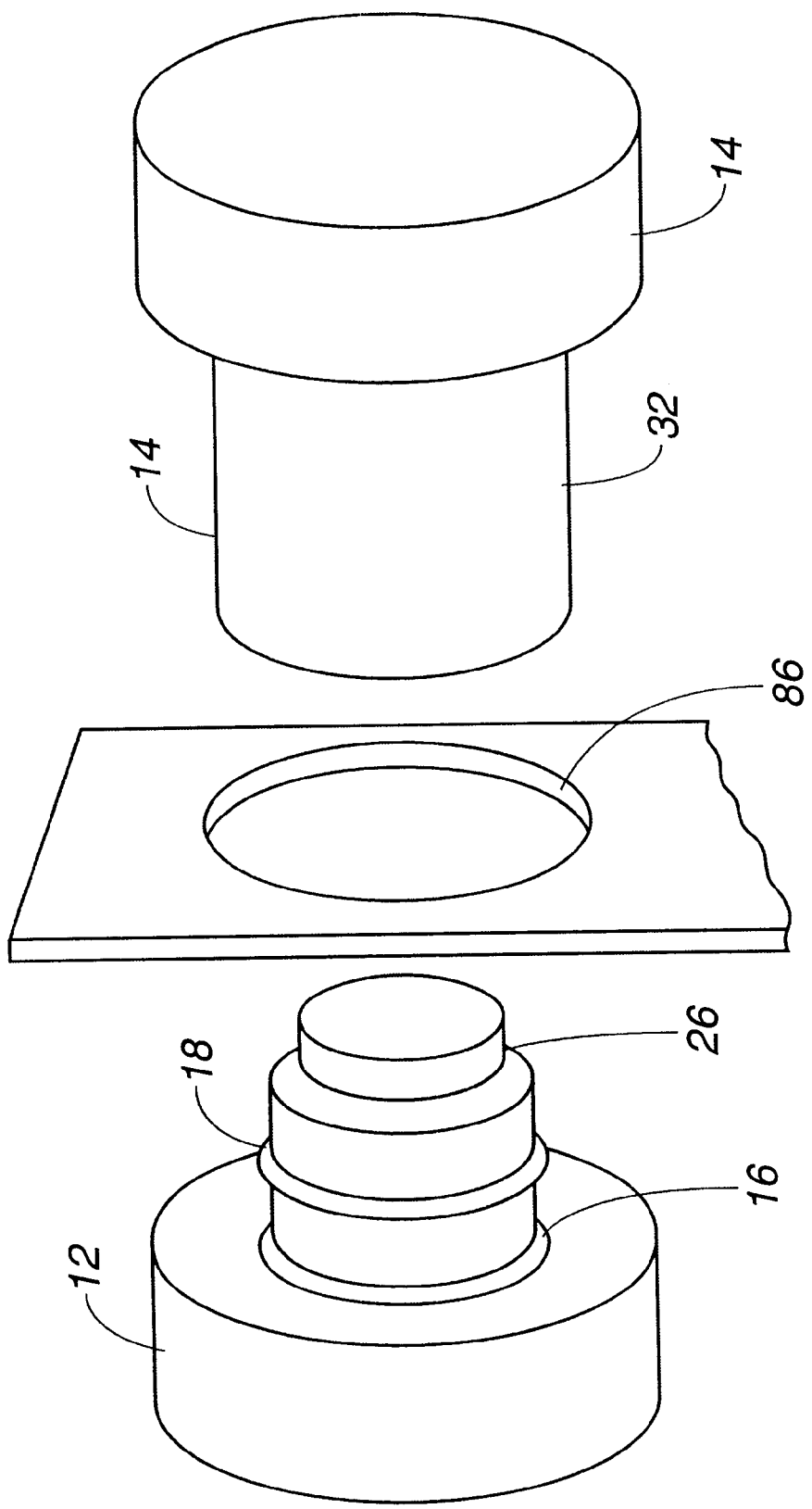
FIG. 7 shows a perspective view of a third embodiment of the present invention prior to installation through the hasp of a container.

FIG. 7 shows a schematic view of the present invention in position for insertion through a hasp. Although the following description refers to device 10, it will be obvious that any of the aforementioned embodiments or their equivalents can be also be used this way. Referring also to FIG. 2, first sealing member 16 and locking ring 18 have been positioned around narrow portion 24 of body member 12. Second sealing member, not shown, can be placed either around end portion 26 or inside hollow portion 34 against wall 38. Attachment may proceeds by inserting second body member 14 through hasp 86, and then inserting narrow end 26 into volume 34 of second body member 14 until first and second body members are attached and cannot be separated without fracturing the device. An optional transparent flexible sleeve, such as a plastic tube, not shown, configured to fit around the device can be slid through the hasp around the device to prevent or attenuate color changes resulting from exposure to sunlight, and also to capture glass fragments after fracture.

Figure 8:
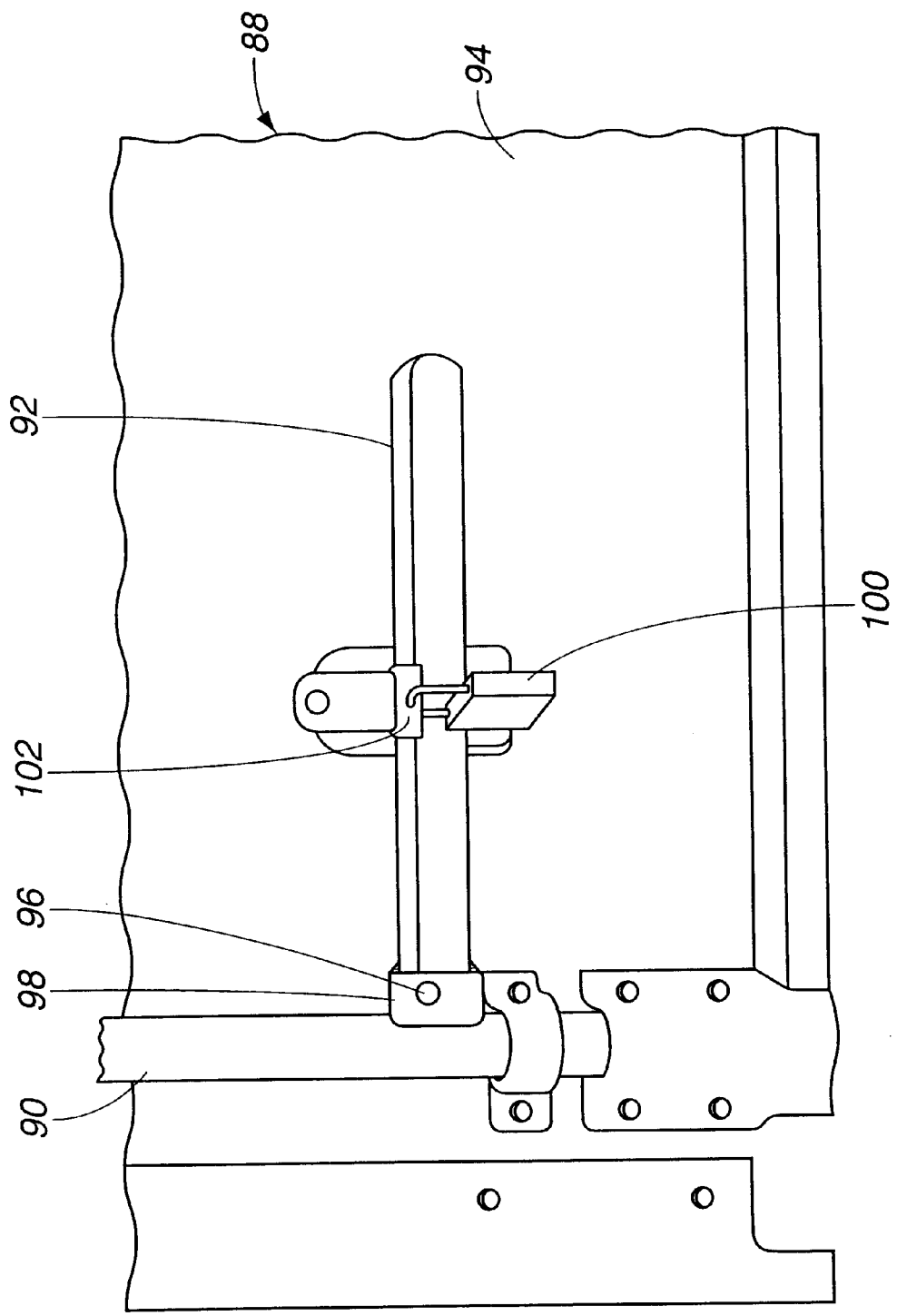
FIG. 8 shows a perspective view of the present invention installed through the locking handle of a transportable container or truck door.

The following example illustrates how the present invention can be used with the locking door handle of a transportable container 88, shown in FIG. 8. A locking mechanism used in many shipping and cargo containers includes vertical locking rod 90 that must be rotated using door handle 92 to open and close container door 94. A rivet 96, typically made of metal, is placed through a hole at one end of the handle. Rivet 96 is attached at both ends to sleeve 98. Sleeve 98 includes coaxial hasps through which rivet 96 passes. Sleeve 96 is connected to locking rod 90. Padlock 100, which could be replaced with the invention or with another type of seal, passes through a hole in door handle 92, not seen, and through hasp 102 that is attached to prevent handle 92 from rotating locking rod 90 to open the door. However, the locking mechanism can be defeated by removing rivet 96, after which door handle 92 can be rotated away from locking rod 90, which can then be rotated to open door 94. Afterward, rivet 96 can be replaced with a counterfeit rivet to avoid detection. The invention can be used in place of rivet 96 and/or padlock 100. If used to replace rivet 96, the design shown in FIG. 4 would be difficult to observe the band structure. Therefore, an embodiment where hollow portions 59 and 72 are skewed with respect to the long axis of the device to allow the bands to be seen when the device is viewed end-on is preferable. The external shape of the present invention can be adapted with relatively flat ends in order to resemble conventional rivets.

Another way to use the invention to create a hasp by drilling a hole through locking rod 90 and to use the invention with this hasp; as the locking rod rotates, one end of the device is forced against the door, which damages and then fractures the device.

There are obviously many ways to verify that the device of the present invention has not been counterfeited. Measurable properties such as light absorption of interior bands, chemical composition of the bands or glass body, could be recorded for future comparisons. A difference in trace impurities in the glass, for example, could indicate that the glass body has been replaced. Highly resolved photomicrographic images of portions of an individual band can be obtained for later comparisons to detect individual particles within that band.

Any attempt to remove the attached device by sawing, cutting, drilling, or otherwise mechanically damaging it will induce fracture into many glass pieces. For embodiments that include internally stored powders, liquids, gels, etc. fracture is accompanied by the release and mixing of these materials. Repairing the damaged device is an almost impossible task. Producing a counterfeit device having the same bands, glass composition, etc. as the original is also extremely difficult. Counterfeiting would require glass blowing skills. Also, glass is a complex material that is difficult to duplicate exactly, or to repair without visible signs of the repair. The device is easily cleaned, will not rust like conventional metal rivets, and is more easily inspected than metal devices that are not subject to inspection without removing them.

A transparent conductive coating can be applied to the inner surfaces of the seal to prevent the use of an external electrostatic field to maintain band patterns during a tampering event. Two-dimensional pictures or other images can also be coated onto the surface of, or embedded within, the device as fingerprint identifiers to make device repair or duplication more difficult.

The above examples of the present invention have been presented for purposes of illustration and description and are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A tamper-indicating device, comprising:
   (a) a locking ring;
   (b) a first glass body member comprising a first end portion, a middle portion narrower than said first end portion, and a second end portion narrower than said middle portion, said middle portion having a circumferential recess for receiving said locking ring;
   (c) a second glass body member comprising a first end portion and a second end portion, said second end portion having an opening leading to an inner hollow volume defined by an inner cylindrical wall and an adjacent wall, said cylindrical wall further including an inner circumferential recess, said second glass body member configured such that when said second end portion and said middle portion of said first glass body are completely inserted inside said hollow portion of said second body, said circumferential recess of said first body and said circumferential recess of said second body are in alignment for receiving said locking ring to attach said first glass body member to said second glass body member.

2. The device of claim 1, said first glass body further comprising an opening in said second end portion of said first glass body leading to a hollow portion within said second end portion extending through said middle portion and through said first end portion.

3. The device of claim 1, said second glass body further comprising an opening in said adjacent wall leading to a hollow volume within said first end portion.

4. The device of claim 1, further comprising;
   (a) materials selected from the group consisting of powders, microparticles, nanoparticles, liquids, gels, or mixtures thereof, said materials being introduced into said hollow volumes within said first glass body member;
   (b) a sealing member for sealing said materials within said hollow portion, said materials providing said device with a fingerprint identifier.

5. The device of claim 1, further comprising;
   (a) materials selected from the group consisting of powders, microparticles, nanoparticles, liquids, gels, or mixtures thereof, said materials being introduced into said hollow volume within said first end portion of said second body member; and
   (b) a plug for sealing said materials within said hollow portion, the sealed materials providing said device with a fingerprint identifier.

6. The device of claim 1, wherein said first glass body member and said second glass body member comprise tempered glass.

7. The device of claim 1, wherein said first glass body member comprises a tempered glass body member.

8. The device of claim 1, wherein said second glass body member comprises a tempered glass body member.

9. The device of claim 1, further comprising an o-ring or gasket sealing member that fits around said middle portion of said first glass body, said sealing member providing an air-tight and moisture-tight seal between said first glass body and said second glass body after said first glass body is irreversibly attached to said second glass body.

10. The device of claim 1, further comprising an o-ring sealing member that fits around said narrower second end portion of said first glass body member, said sealing member providing an air-tight and moisture-tight seal between said first glass body and said second glass body after said first glass body is irreversibly attached to said second glass body.

11. The device of claim 1, further comprising means for generating a positive pressure within said first glass body.

12. The device of claim 11, wherein said pressure generating means comprises:
    (a) a coil spring configured to fit through the opening and inside said hollow volume within said first glass body; and
    (b) means for restraining said coil spring when said coil spring is in a compressed state.

13. The device of claim 11, wherein said pressure generating means comprises a solid or liquid material that is sealed inside said first glass body member, said material subsequently generating a gas that produces an internal pressure within the glass body.

14. The device of claim 11, wherein said positive pressure is generated by cooling said first glass body prior to use.

15. The device of claim 1, further comprising means for generating a positive pressure within said second glass body.

16. The device of claim 15, wherein said means for generating a positive pressure within said second glass body comprises:
    (a) a coil spring configured to fit through the opening in said adjacent wall and inside said hollow volume within said first end portion of said second glass body member; and
    (b) means for restraining said coil spring when said coil spring is in a compressed state.

17. The device of claim 15, wherein said means for generating a positive pressure comprises a solid or liquid material that is sealed inside said second glass body member, said material subsequently generating a gas that produces an internal pressure within the glass body.

18. The device of claim 15, wherein said means for generating positive pressure within said second glass body comprises cooling said second glass body prior to use.

* * * * *